United States Patent [19]

Ketler et al.

[11] Patent Number: 5,420,440
[45] Date of Patent: May 30, 1995

[54] OPTICAL OBSCRUATION SMOKE MONITOR HAVING A SHUNT FLOW PATH LOCATED BETWEEN TWO ACCESS PORTS

[75] Inventors: Albert E. Ketler, Murrysville; Christopher Kolesar, North Huntingdon, both of Pa.

[73] Assignee: Rel-Tek Corporation, Monroeville, Pa.

[21] Appl. No.: 202,565

[22] Filed: Feb. 28, 1994

[51] Int. Cl.⁶ .............................................. G01N 15/06
[52] U.S. Cl. ..................... 250/573; 356/438; 340/630
[58] Field of Search ............... 250/573, 574, 575, 239; 356/338, 438, 439; 340/630, 628

[56] References Cited

U.S. PATENT DOCUMENTS

| | | |
|---|---|---|
| 3,500,450 | 3/1970 | Payton et al. . |
| 3,544,218 | 12/1970 | Cassidy ................. 250/573 |
| 3,708,675 | 1/1973 | Tashiro et al. . |
| 3,976,891 | 8/1976 | Parkinson . |
| 4,099,065 | 7/1978 | Malinowski . |
| 4,129,383 | 12/1978 | Malinowski ............ 250/574 |
| 4,269,510 | 5/1981 | Horvath et al. . |
| 4,384,488 | 5/1983 | Scheidweiler . |
| 4,543,815 | 10/1985 | Troup et al. . |
| 4,906,978 | 3/1990 | Best et al. . |
| 5,021,677 | 6/1991 | Igarashi et al. . |
| 5,170,150 | 12/1992 | Austin et al. . |
| 5,247,283 | 9/1993 | Kobayashi et al. . |

Primary Examiner—David C. Nelms
Assistant Examiner—Que T. Le
Attorney, Agent, or Firm—Browdy and Neimark

[57] ABSTRACT

An obscuration type optical smoke monitor is provided for use particularly in dusty and dirty environments. The smoke monitor comprises a housing enclosing a smoke monitoring chamber; two access ports located opposite each other on the housing; a shunt air flow path located between said two access ports; means to conduct air from said access ports through an optical chamber; a light emitting diode at the first end of said optical chamber, which light emitting diode produces a light beam axially through the center of said optical chamber; a photo transistor at the second end of said optical chamber to receive the light bean and issue an electrical signal proportional to the received light intensity; and an electronic module which provides variable electronic output, generating an analog output essentially proportional of the optical obscuration caused by the smoke. Baffle means are provided to minimize extraneous light scattering from dust and dirt in the air,

26 Claims, 7 Drawing Sheets

OPTICAL OBSCRUATION SMOKE MONITOR HAVING A SHUNT FLOW PATH LOCATED BETWEEN TWO ACCESS PORTS

FIELD OF THE INVENTION

The present invention is directed to an optical smoke monitor which can be used in environments where dusty conditions prevail. Smoke monitoring is considered an alternative to carbon monoxide monitoring which is subject to interference from false alarms, diesel machinery and other CO sources.

BACKGROUND OF THE INVENTION

In many heavy industries and in mines, there is much dust in the air. Federal standards for early warning of fires in mines use an obscuration standard rather than particle ionization or particle reflection technology. Unfortunately most optical devices are expensive because of their short life in dusty and moist environments. Some smoke detection devices use high levels of radioactive materials to avoid dust accumulation and are hazardous because of the radiation.

Smoke monitoring is essential in many industries in which smoke is generated without much carbon monoxide, which is commonly monitored. For example, compressor overheating, conveyor belt slippage, electrical equipment faults and other types of overheating incidents, particularly involving plastics, can produce a great deal of smoke but minimal amounts of carbon monoxide. In many industries using heavy equipment, the above incidents may generate thick, choking smoke, while there is no activation of a conventional temperature of carbon monoxide sensor and alarm. Compared with point heat (temperature) sensors, carbon monoxide sensors are invaluable for early detection of spontaneous combustion of coal and wood. However, smoke monitoring is necessary to detect fires with low heat and low output of carbon monoxide.

Conventional smoke detectors cannot be used in dusty conditions because of false alarms and clogging with dust. The U.S. Department of the Interior, Bureau of Mines, tested technologies using light scattering and ionization, as well as air pumps to convey the gas sample to the detection device, reference IC 9311. Unfortunately, although these devices detected some actual smoke-forming events, false alarms were frequent.

Additionally, acetylene and hydrogen gases interfere with carbon monoxide sensors. Moreover, most carbon monoxide sensors are temperature sensitive, and there are maintenance problems involved in establishing an ambient level of carbon monoxide. Conventional carbon monoxide sensors require costly calibration gas, have a short cell life, and these sensors are inclined to drift.

U.S. Department of the Labor, Mine Safety and Health Administration (MHSA) regulations permit either a carbon dioxide or a smoke sensor for fire monitoring of underground electrical sites. Among the federal 30 CFR regulations relating to smoke monitors are:

75.340 (a) Underground electrical installations, monitor intake air for carbon monoxide or smoke; 5% per meter smoke alarm level; functional test every 31 days. Although carbon monoxide or smoke sensors are permitted, the sensitivity to hydrogen gas discounts carbon monoxide if battery chargers are involved.

75,344 Compressors: specifies carbon monoxide or smoke.

75,351. Atmospheric monitoring systems: smoke alarm set at 0.05 per meter (5% obscuration); electrical equipment, such as transformers, battery chargers, substations, rectifiers, or water pumps, site at least on sensor (carbon monoxide or smoke) 50-100 feet in the direction of air flow; functional testing every 31 days. Only one alarm level is specified for smoke, compared with two alarm levels for CO, although the analog smoke monitor can control visual warning devices in the same manner as a carbon monoxide sensor.

The MSHA standard prescribes a light absorption value that does not correlate easily with ionizing figures. Light obscuration has little correlation with the degree of particle ionization. Given a level of smoke obscuration from a real fire, of approximately a 5% alarm level, the actual degree of particle ionization produced depends greatly upon the source of the smoke, including the intensity of the fire, the materials involved, the air velocity, oxygen concentration, and the like. These variables are not normally known, controlled, or monitored. Therefore, inferring the level of obscuration corresponding to a measured ionization level is highly complex, and is certainly not a linear and faithful relationship. The dilemma the user faces is that the ionization warning and alarm levels chosen can result in noncompliance with the optical obscuration standard under the worst case combustion conditions. Otherwise, the ionization alarm levels must be set so low as to be impractical, resulting in false alarms and sensitivity to dust.

Moreover, most smoke detectors are just that—"smoke detectors," and merely indicate an alarm or no alarm (smoke or no smoke) condition. An ionizing smoke detector has no analog output, and alarms tend to be inconvenient surprises, with no prior warning of impending problems. If an ionizing smoke detector becomes contaminated with dust, generally the only option is to remove the detector from the mine, and to return the detector to the factory for repair.

Prior workers have sought to provide smoke sensors that can function in dusty environments, but all of them have some drawbacks.

Kobayashi et al., in U.S. Pat. No. 5,247,283, disclose a smoke sensor which can be used in a dusty environment and which can be tested to ensure that it is operating properly. A light beam which is emitted from a main light emitting element and is scattered in an interior sensing space is received at a main light receiving element, and an output signal responsive to the quantity of light received at the main light receiving element is processed at a signal processing circuit for sensing the presence of smoke or dust particles. A second output of an auxiliary light receiving element for the emitted light directly received from the main light emitting element and a composite output of the first and second output are compared. An alarm is generated when the level of output is other than a predetermined amount. In this case, dust interference is eliminated by providing a net. There is no indicator of smoke other than an alarm.

Best, in U.S. Pat. No. 4,906,978, disclose an optical smoke detector of the Tyndall type which measures light scattering. In this type of detector, smoke particles are admitted into a closed smoke chamber while outside ambient light is precluded from the chamber. A light beam projected into a test zone of the chamber will strike and bounce off of dust or smoke particles in the test zone to produce scattered or diffused light which is then detected by a photo or light responsive sensor to indicate the presence of an alarm condition. In the absence of dust or smoke particles, the light responsive sensor is optically shielded from the light source. At least one of the surfaces of the smoke chamber is shaped to provide a series of parallel grooves for accumulating undesired dirt and dust in the groove crevices and for minimizing the reflection of light from that dirt and dust and toward the radiation sensing means, thereby to preclude false alarms.

Scheidweiler, in U.S. Pat. No. 4,384,488, discloses a smoke detector containing at least one smoke measuring chamber which possesses a mounting or socket plate for mounting on the ceiling of a room, and a housing enclosing the smoke measuring chamber and suspendingly secured at the socket plate. Openings in the housing permit entry of ambient air. The air entry openings can be changed to account for dust in the air. Protuberances or projections can be included in the inlet to cause deflection of the incoming or entering air. The cross-sectional area of the air entry opening can be adjusted to reduce interference from dust particles. In this case, the smoke sensing element itself is an ionization type, not optical.

Horvath et al., U.S. Pat. No. 4,269,510, disclose a smoke detector for a fire alarm comprising a nuclear radiation source possessing a substantially conical ring-shaped radiation characteristic or pattern and a radiation receiver arranged along the axis of the radiation source but externally of the direct radiation. The radiation receiver receives radiation which is scattered by smoke particles within the conical ring-shaped radiation region. To reduce the spurious radiation impinging on the radiation receiver the radiation region is bounded by elements located externally of the direct receiving region of the radiation receiver. Web means are provided which are shaped to prevent dust from collecting on their radiation receiving surfaces to minimize the effects of dust.

Malinowski, in U.S. Pat. No. 4,099,065, discloses a smoke detector operating on the principle of reflected light. Smoke inlet slots are provided between the light and photo-cell recesses which prevents accumulation of dust and dirt therebetween which could cause a false alarm.

Igarashi et al., U.S. Pat. No. 5,021,677, disclose a light scattering-type smoke detector comprising a dark box which is surrounded by a labyrinth around its outer periphery that is internally provided with a light projection element and a light receiving element. A test lamp using a light emitting diode is surrounded by light-shielding columns. The light-shielding columns each have a J-shaped configuration which constitutes part of the labyrinth surrounding the test lamp. In a normal state clean air containing no smoke particles flows into the dark box and light from the light projecting element is nor received by the light receiving element. This device uses scattered and reflected light to detect smoke.

Payton et al., in U.S. Pat. No. 3,500,450, disclose an optical device for the examination of smoke and dust laden gas consisting of two colinear tubular portions connected together by a support member. One tubular portion contains a light source and the other tubular portion contains a light-sensitive device. Smoke or dust-laden gas is arranged to pass upwardly between the tow tubular portions and thus between the light source and the photo-sensitive device. Baffles are inserted into each tubular portion to prevent dust or dirt particles form being deposited either onto the light source or onto the photosensitive device.

Tashiro et al., in U.S. Pat. No. 3,708,675, disclose a smoke detector in which air entrance and egress are located in oppositely disposed surfaces. The air flow passages are arranged so as to cause the air to flow at different velocities. When there is smoke present in the air, the velocity difference in the air flow creates a difference in static pressure that aids in introducing smoke into the casing.

Austin et al., in U.S. Pat. No. 5,170,150, disclose a smoke detector which incorporates therein means for verifying the detector's smoke sensitivity limits. This means includes positively positioning various light reflecting surfaces to provide predetermined light reflection onto light sensing means to create simulated smoke levels.

None of the above-noted smoke detectors is designed to work in a particularly dusty or dirty environment such as a coal mine. Furthermore, none of the above smoke detectors responds to the primary legal fire alarm parameter, namely, the obscuration of a beam of light. The reflected light devices bear the same ambiguity as the ionizing particle devices, namely, correlating the sensor output with the primary legal requirement, the percent obscuration of a light beam. The amount of light reflected from smoke of a given light obscuration level is influenced by the color of the smoke, the particle size and distribution, the degree of turbulence in the optical chamber and other parameters which make a direct correlation with the optical obscuration standard extremely complex, if not impossible.

SUMMARY OF THE INVENTION

The present invention overcomes the aforesaid deficiencies in the prior art.

It is an object of the present invention to provide an optical smoke monitor which electrically monitors and compensates for errors caused by the accumulation of a dust film on the optical components of the monitor, thus avoiding drifting and false alarms.

It is another object of the present invention to provide an optical smoke monitor which admits smoke laden air preferentially to the optical chamber, thus minimizing entry of dust which would cause errors in smoke level determination.

It is a further object of the present invention to provide an optical smoke monitor which minimizes the effects of dust particles deposited by gravity within the optical chamber of the monitor from causing errors by altering the reflectivity of the chamber walls, without overly restricting flow of air or smoke through the chamber.

It is yet another object of the present invention to provide an optical smoke monitor having optical surfaces which are easily cleaned of dust accumulations.

It is still another object of the present invention to provide an optical smoke monitor which optically and electrically senses the optical clarity of a mixture of smoke and air and which converts this to an analog electrical signal which can be monitored remotely through external devices.

It is a further object of the present invention to provide an optical smoke monitor which includes means to admit smoke laden air into the optical sensing path thereof by diffusion alone, using low velocity ambient air movements, thus eliminating the need for an air pump or fan.

It is still another object of the present invention to provide an optical smoke monitor which includes means to passively separate larger and heavier dust particles from an air sample which is laden with smoke introduced into the optical path, thus minimizing false alarms from the optical absorption of dust, accomplishing this without the need for filters which can clog and require frequent cleaning.

It is still another object of the present invention to provide an optical smoke monitor which reduces power consumption through unique electronic circuitry such that the entire smoke monitoring device is intrinsically safe and can be installed in hazardous areas.

It is yet another object of the present invention to provide field settable threshold detection circuitry to monitor the analog signal level, and which can be used to actuate external warning and alarm devices.

It is a further object of the present invention to provide an optical smoke monitor in which a calibrated optical filter is introduced into an optical light beam for periodic calibration, simulating smoke, so that a quick and accurate full scale reading can be obtained.

It is still another object of the present invention to provide an optical smoke monitor which includes means for electronically performing a calibration by functionally testing the unit between full calibration events merely by depressing a switch.

It is yet another object of the present invention to provide an optical smoke monitor which can be assembled into a light chamber in which the direct light is maximized and the reflected light is minimized, and which amplitude of the direct light beam can be monitored electronically, simply, reliably and at low cost.

It is still another object of the present invention to provide an optical smoke monitor which can be rotated out of its normal, stowed operating position inside an enclosure or housing for easy access for cleaning, calibrating, and other maintenance.

It is a further object of the present invention to provide an optical smoke monitor in which the effects of large ambient air velocities are prevented from propelling dust into the optical chamber without the use of mechanical filters.

It is yet another object of the present invention to provide an optical smoke monitor which can prevent massive intrusion of dust while rock dusting in coal mines by temporarily plugging the smoke/air access ports of the device.

According to the present invention, a smoke monitor is provided which electrically monitors and compensates for errors caused by accumulation of dust film on the optical components. A passive diffusion photoelectric beam absorption is used which includes specially designed baffles and electronic means to overcome the problems with dust interfering with smoke monitoring.

The smoke monitor of the present invention eliminates cross interference problems common to carbon monoxide sensors when they encounter hydrogen and acetylene present in mine environments, avoids the temperature sensitivity of electrochemical carbon monoxide cells, and avoids maintenance problems associated with establishing an ambient level of carbon monoxide. The smoke monitor of the present invention also provides smoke monitoring without costly calibration, short cell life, or drift.

The device of the present invention includes a built in optical filter to provide a field calibration reference, thus avoiding the need for a smoke source to calibrate. The zero smoke point can be set when the ambient air is obviously and visibly clear. Shining a light beam (as from a miner's cap) down the area or room to be monitored without observing a halo is sufficient evidence of zero smoke conditions to permit adjustment of the instrument to read zero, or 4 ma. To simulate full scale smoke, the optical filter cap is moved into the calibrate position, such as by rotation, depression of the closure device, etc. and the span is adjusted (full scale) output to read 20 ma.

The optical smoke monitor of the present invention responds directly to the alarm level for obscuration specified by law, and thus can be used with confidence that the monitoring provides sufficient and reliable warning of dangerous conditions.

DETAILED DESCRIPTION OF THE INVENTION

The optical smoke monitor of the present invention provides a "monitor" or "sensor" rather than a "detector" for smoke, enabling one to monitor the amount (optical obscuration) of smoke on location and to monitor any change in smoke levels. This monitor has an analog output which is proportional to the input parameter, i.e., the optical smoke density. The output of one embodiment of the invention is 4-20 ma, which is linearly proportional to the visual obscuration, the basic MSHA standard for smoke monitoring in underground mining. Of course, the output of the monitor can be varied depending on the required sensitivity of the monitor and conditions to be monitored.

Although the present optical smoke monitor was originally developed for solving a particular problem associated with underground coal mining, wherein horrendous dusty conditions combine with the severe fire hazards and the MSHA's visual obscuration law to preclude the practical use of alternative smoke monitoring devices, the optical smoke monitor can be used in a variety of environments where monitoring of smoke is desirable or necessary. One of the advantages of the optical smoke monitor of the present invention is that an external electronic monitoring system can continuously monitor many sensors and activate alarms which are remote from the actual sensor. As one skilled in the art can readily appreciate, the optical smoke monitor can easily be adapted for use in other environments by adding a power supply, a threshold detector, and a suitable alarm device, such as a horn, a visual strobe, or the like. One skilled in the art can readily ascertain what modifications can be made to the optical smoke monitor to make it particularly useful at manufacturing sites, foundries, chemical plants, refineries, parking garages, vehicles (buses, trains, aircraft, boats, ships, etc.), barns, furnace rooms, and commercial and retail establishments including restaurants, taverns, shopping malls, and the like. The optical smoke monitor of the present invention is particularly well suited to environments in which it is normal to have heavy dust, ionized vapors, interfering chemicals, carbon monoxide (e.g., from auto exhaust), ionized gases, and/or high temperature which cause false (non-fire) alarms with ionizing, carbon monoxide, heat and other types of conventional fire detectors.

Mines in which diesel powered machinery is used experience frequent false alarms on conventional carbon monoxide fire monitoring and detecting systems, as these sensors respond to the carbon monoxide in the diesel exhaust. The smoke monitors of the present invention present a highly beneficial alternative to carbon monoxide monitoring by avoiding alarms based solely on carbon monoxide levels, while the smoke level is sufficiently low to avoid false smoke alarms. As noted above, because of the historical sensitivity to dust, smoke monitors have not previously been used. The optical smoke monitor of the present invention, however, now provides a safe, reliable monitor for smoke that is not interfered with by dust, hydrogen or carbon monoxide in the air.

The optical smoke monitor of the present invention can be easily cleaned and recalibrated to its original condition in a few minutes, using a simple tube brush. The analog output of the monitor makes even slight changes in observation level readily apparent, triggering immediate investigation and remedial actions even before an alarm is activated.

The smoke monitor of the present invention uses a passive photoelectric beam absorption scheme using special baffles and electronic means to overcome problems associated with conventional smoke detectors. The optical smoke monitor of the present invention enjoys a high degree of stability underground in mines, even given the large amounts of dust, dirt and moisture present in most mines.

Figure 1A:
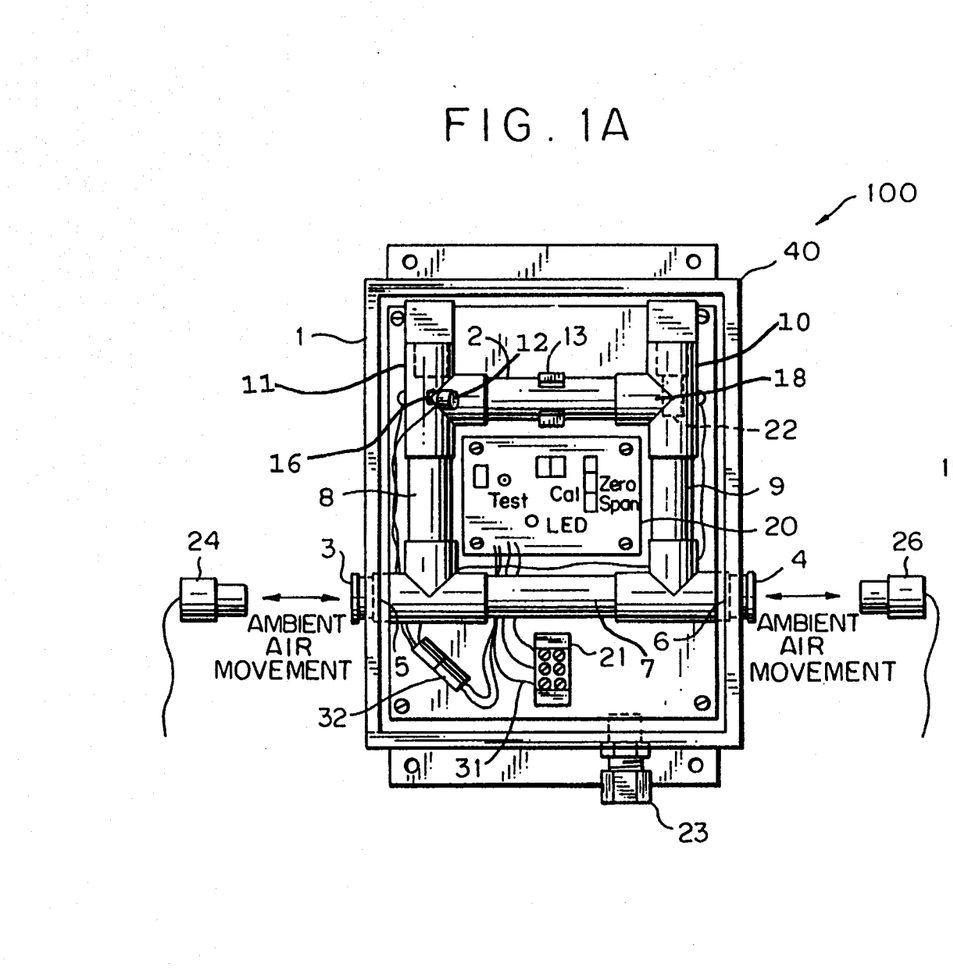
FIG. 1A shows a front view of an optical smoke monitor according to the present invention.

Referring to FIG. 1A, the monitor of the present invention 100 is normally installed in a vertical attitude, mounted onto a wall of the area to be monitored. Air laden with smoke and dust diffuses into and out of the two access ports 3 and 4, one aimed outwardly on each side of the unit. Each access port, which is generally from about ¼ to 1 inch in diameter, expands immediately inside the access fitting at 5 and 6, respectively, to about double its original diameter, thus reducing the air velocity to approximately one fourth that of the inlet air velocity. A screen 5 and 6 on the inside end of the access fitting further slows the air flow and prevents large particles from entering. The lower stream velocity in the inside pipe fitting is less able to propel the heavier dust particles, so most of these particles fall to the bottom of the pipe. A shunt flow path 7 connecting the two access holes permits the majority of the air to flow directly through the unit and out the other side with minimum pressure drop inside. In the event that the unit is located in a high velocity path, such as in a ventilation duct, the shunt path conducts any large volumes of air/dust/smoke directly through the unit, discharging it from the opposite access port.

As the air flows through the unit, a very small pressure differential occurs between the upward leading pipe fittings 8 and 9 on each side of the shunt flow path. The vertical path components of fitting 8 and 9 on either side of the shunt flow path therefore conduct a small aerosol (air/smoke) component of the total inlet flow crossing through the horizontally oriented light chamber 2, and then downward on the opposite side of the light chamber 2 to mix with the cross flow component for discharge. Two push-on pipe caps 14 and 15 at the top of each vertical sample flow stack 10 and 11 prevent leakage of the sample stream from the essential optical path. The time dwell during the vertical ascent of the minute sample flow provides additional separation opportunity for heavier dust particles to fall by gravity from the sample flow. The flow direction depends on the direction of ambient air flow outside the instrument, as well as the orientation of the unit with respect to this ambient flow, as the flow components are identical for either side.

A light source, such as an infrared light emitting diode (LED) 16 on the left end of the optical chamber 2 produces a narrow beam of light axially through the center of the optical chamber 2. A radiation sensing means or photo receiver, as exemplified by but not limited to a photo transistor 18 on the right end of the optical chamber receives the light beam and issues an electrical signal proportional to the received light intensity. As more smoke obscures the light beam, the electronic module 20 causes the output to vary, generating an analog output essentially proportional to the light absorption (optical obscuration) caused by the smoke.

The signal from the photo-transistor 11 is transmitted to the electronic circuit contained in the module 20, which is encased in conventional potting material. As more smoke obscures the flow path 2, more light is absorbed and the light intensity received by photo-transistor 11 is reduced proportionately. The electronic module interprets this diminished signal as an increased smoke level and, in turn, generates a 4–20 ma analog output, the output proportional to the optical obscuration in the light chamber. This 4–20 ma signal is monitored externally using a meter, recorder, computer, or other device, which, in turn, generates warning or alarm signals at predetermined thresholds at any desired remote locations for monitoring. One example of a conventionally useful threshold is 5% obscuration. The instrument can be calibrated so that the full scale output occurs at 10% obscuration, so that the federally mandated 5% alarm point occurs at mid-scale. Alternatively, if external monitoring equipment is not available or practical, as with a single, stand-alone smoke monitor, field settable threshold detection circuitry is included in the electronic module for activating signal means such as a horn or bell or strobe light which may be attached to the instrument or connected externally at some remote location. An analog or digital meter may be installed on the front of the unit to display the percent obscuration visually.

As an example, clear air absorbs very little light, and the electrical output is set at 4 ma the analog for zero smoke. If the smoke intensity increases to 10% per meter obscuration, the electrical output reads 20 ma, the analog for full scale 10% per meter.

Dust plugs 24, 26 are provided for sealing the two access ports, 3, 4, respectively, when particularly dusty conditions prevail, such as rock dusting in underground mines. It is important to minimize the intrusion of large quantities of dust, which can collect on the optical surfaces and alter the accuracy of the smoke monitor. After the dusty conditions are over, the dust plugs are removed to enable the sensor to return to its smoke sensing function.

Figure 1B:
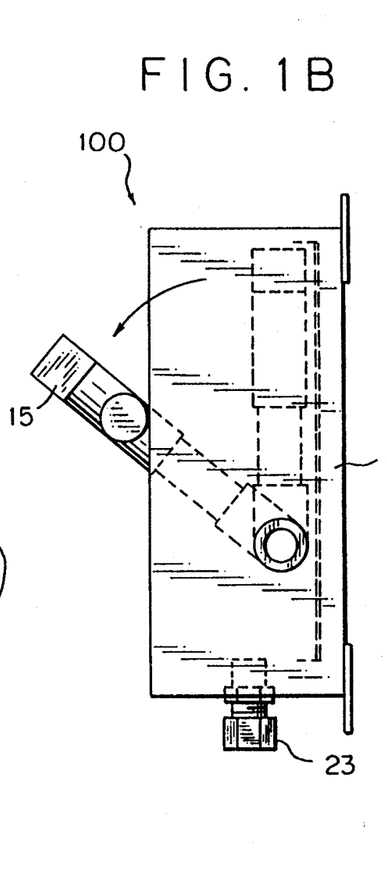
FIG. 1B shows a side view of an optical smoke monitor according to the present invention.
Figures 2A, 2B:
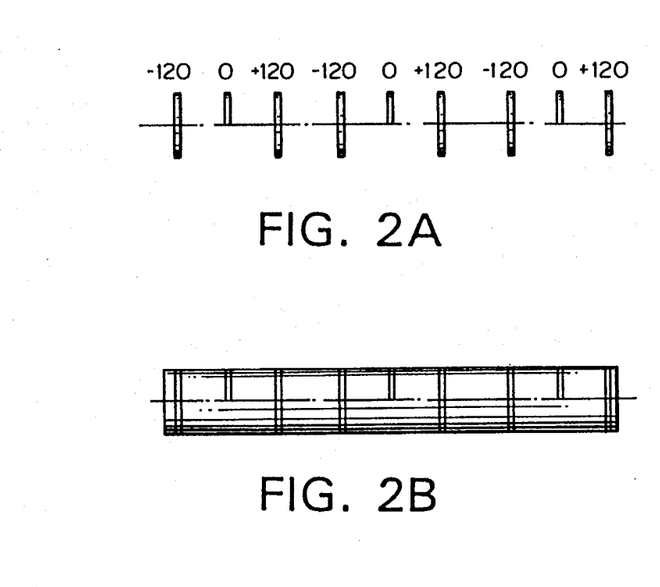
FIGS. 2A-C show the orientation of washers and baffles in one embodiment of the smoke monitor of the present invention.
Figure 2C:
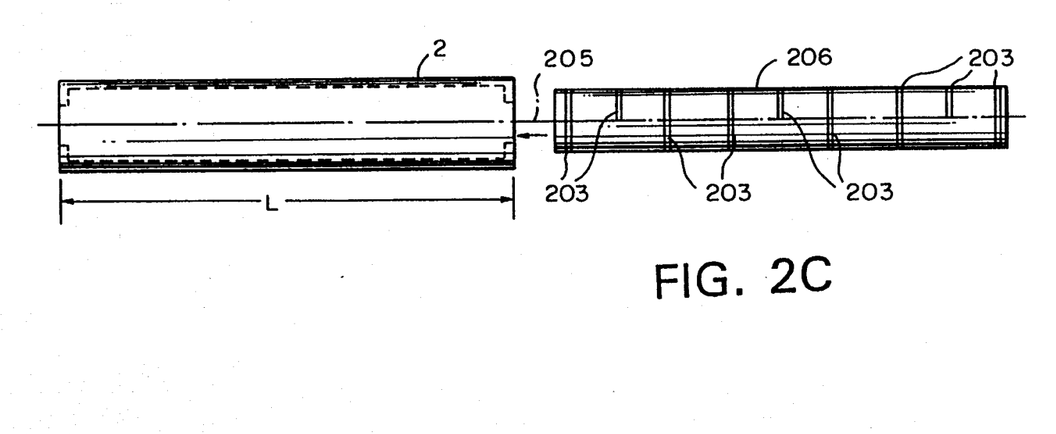
Figure 2D:
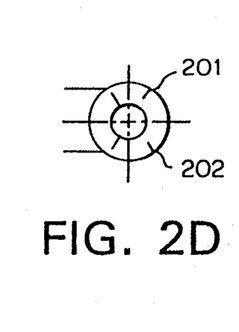
FIGS. 2D-F are front views of FIGS. 2A-C.
Figure 2E:
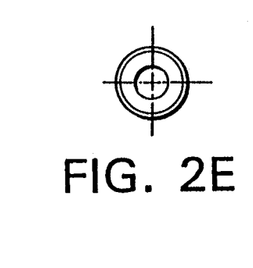
Figure 2F:
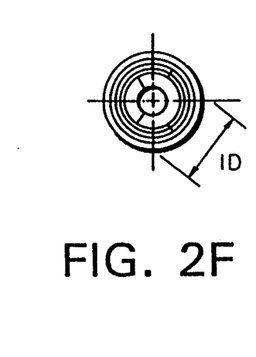

Although the smoke monitor of the present invention is designed specifically to reduce dust sensitivity, if a buildup of dust or haze occurs on the internal optical surfaces, the sensor can be easily cleaned. The device should be rotated downward as shown in FIG. 1B. The caps are removed form the ports 14 and 15, and a brush is inserted and moved up and down. The brush can be sprayed with window cleaning solution to assist in removing greasy buildup. After cleaning, remove the brush and replace the caps. The device is then recalibrated by turning the calibrating cap into the "run" position and adjusting the zero point for a precise 4.0 ma output. The calibrating cap is returned to the "cal" position, and the span pot is set to read 20 ma. The calibrating cap is then returned to the "run" position to resume operations.

The Code of Federal Regulations, CFR 30, part 75.351(4), specifies 5% per meter obscuration as the alarm level for underground coal mines. Thus, the optical smoke monitor is set at 10% per meter full scale, thus placing the specified alarm level threshold at mid scale. A potentiometer in the circuitry provides means to adjust the effect of the optical filter whenever introduced into the light beam, so that its light absorption corresponds precisely with 10% full scale output.

To compensate for eventual and inevitable film buildup on the optical emitter and receiver, a short range reference radiation sensing means, such as a photo transistor receiver 12, monitors the optical intensity of the light beam immediately as emitted from the LED. Should the optical surfaces (LED and photo transistor) become contaminated, the sensed light intensity is inclined to drop. The electronic circuitry receives this reference signal and drives the LED more or less to maintain a constant optical path correction. Since the receiver 12 is very close to the emitter, generally around 0.25 to 1.5 inches, smoke obscuration to this device is negligible. Thus any changes must be due to contamination, LED aging, or other non-smoke related changes in the optical and electrical system. The negative feedback concept assures a constant, stable optical beam that is oblivious to the effects of dust and temperature, thus permitting smoke obscuration to be monitored with minimum error from extraneous factors.

As is readily apparent to one skilled in the art, the light source may be any source of light which can be used within the confines of the smoke monitoring device. This light source may be chosen from among light sources that can be received by the photo receiver on the opposite side of the optical chamber. In a similar fashion, the photo receiver or radiation sensing means is not limited to a photo transistor, but may be any type of receiver which is compatible with the other components of the smoke monitor of the present invention. One skilled in the art can readily determine without undue experimentation alternative light sources or light sensing means which can be used in this device.

Eventually, and inevitably, some dust particles will accumulate in the optical chamber. Since dust is largely light in color, any deposits on the side walls of the optical chamber can cause sparious light reflections which can be received by the photo transistor 11. These light reflections may be misinterpreted as a reduced smoke intensity (i.e., higher than the true light intensity). Therefore, it is imperative to baffle the optical chamber in such as way that substantially all reflective surfaces are eliminated.

A number of baffling techniques were tested for their efficacy in eliminating reflective surfaces. When black flock was bonded to the inside walls of the chamber, too much surface area was presented to the radiation sensing means, so this was rejected as being useless. Another method involved using thin disks with centrally punched holes (similar to washers), the disks oriented so that the beam passed through the central holes. Three disks were spaced along the light path, one at each end of the chamber and one in the middle. Unfortunately, the disks greatly reduced the flow area, thereby stifling the movement of the air/smoke mixture through the chamber. The response time became unacceptably long, taking as much as one half hour to stabilize at a specific ambient smoke level.

The problem of baffling was solved by using baffles which blocked side wall reflections while not significantly obstructing the flow of diffused air. As shown in FIGS. 2A-F, thin disks 201, similar to washers, were cut in halves, and the halves inserted at three intervals along the length of the light chamber 2 (FIG. 1A). Three half disks were stationed at each end and at the middle, for a total of nine half disks. Using three half disks instead of two permitted a 60 degree angular overlap at the cut ends of the disks, thus avoiding the need for precise alignment or risking end light leakage. Before cutting the disks diametrically in two, the edges of the central hole 202 in each washer were chamfered, which presented a sharp edge to the light beam directed through the half disks, thus minimizing any horizontal surfaces for dust to accumulate and from which reflections could occur. The least number of half disks to be used should be the number required to minimize the number of edges in the light beam. Using a larger diameter chamber could eliminate the need for the center station, reducing the number of required disks to six, since the chamber walls would be out of range for reflections. However, a larger chamber would require more smoke to fill, and the entire instrument would grow in size as the inlet ports would have to be expanded to admit the necessarily larger volumes of air/smoke flow. Although the geometry is not restricted, a chamber of approximately ⅞ inch diameter by five inches in length was found to be a practical size.

In one embodiment of the present invention, the chamber is circular. However, the chamber can be of any cross sectional shape, size and length to function as an optical smoke monitor according to the present invention. However, the response time, sensitivity, size, weight, ease of cleaning, packing and the like would vary. Baffles must obstruct all light paths except the one directly through the center, and must accomplish this obstruction without presenting reflective surfaces. The baffles can be of any shape. However, ideally, the baffles should approximately conform to the shape of the chamber in order to minimize light transmission. The baffles should preferably be very thin or at least have thin or sharpened edges to eliminate horizontal reflecting surfaces. The baffles can be made of any material, so long as they can be readily fabricated and assembled, while maintaining their prescribed positioning. Examples of materials of which the baffles can be made are aluminum, brass, or other rigid non-corroding sheet metal, as well as glass, ceramics or plastics. Indeed, in large production, the entire optical chamber can be injection molded or or otherwise encased, thus reducing costs. Since low reflectance surfaces are desired, a dull black paint, flock, or other matte surface is desirable.

It should be noted that an effective baffle is necessary for successfully measuring extremely small changes in light level over the short (typically about five inches) optical path. The federal obscuration specification of 5% per meter translates to a mere 0.7% in five inches. Although it would seem that a longer path would give a stronger smoke signal, this is offset by the lower intensity of the received signal at the low 3–4 ma LED current needed to achieve long term source stability. Thus, it was found that longer distances actually resulted in weaker received signals and lower net smoke sensitivity. In view of the small signals involved, any reflected portion of the light arriving at the photo-transistor which is subject to variation due to changes in surface reflectivity from dust results in a large amount of drift and error. Without a baffle, any dust accumulations would mask the desired smoke absorption signal, thus confusing and biasing the electronics. Since it is impossible to completely eliminate the presence of some amount of dust, the present inventors took the alternative approach of eliminating essentially all reflecting surfaces. The principles for designing a perfect baffle, i.e., one with no reflections or flow restrictions, were discovered by the present inventors. The only variation is in implementation of the baffles.

In one embodiment of the baffle means, shown in FIG. 2, nine half disks 203 were installed at 0, +120 and −120 degrees alternately along the chamber length, providing overlapping light baffling. In other words, the photo transistor received no reflective components of light from the walls of the optical chamber. Ideally only light through the center aperture 205 reaches photo transistor 11. A small pipe 206 with nine diametrical cuts, such as one having a diameter slightly less than the inner diameter of the optical chamber 2, was used as a holder for the disks. The disks were assembled, aligned and epoxy bonded on the back, and the complete assembly was then inserted and finally bonded into the optical chamber 2.

The air flow through the chamber went up, down and around the half disk segments, baffling the light, while permitting the air to flow substantially unimpeded. The half washer baffles restricted the cross sectional flow area by about 50%, although less than 50% restriction is not essential since only the response time is affected. Higher restriction slows down the response, while lower restriction speeds up the response. It was found that 50% restriction permitted a time constant of about 30 seconds, which was sufficiently fast for fire detection, but which was a compromise with the faster response that could have been achieved with lower restriction. However, the blocking of reflected light must be accomplished, regardless, or the instrument will be sensitive to dust accumulations and prone to gradually drift downward, indicating lower smoke levels than is actually the case. Increasing the number of baffles is self defeating, as the number of reflecting edges increases, and the flow restrictions increase, both negative effects. On the other hand, reducing the number of baffles below the three stations of three (nine), permits light reflections from the chamber walls which generates prohibitive dust sensitivity and drifting. A helical baffle made of thin sheet metal or plastic can also be used successfully. However, the fabrication of a helical baffle is more difficult than with some other configurations, as the helical baffle requires segmenting and bonding of split rings or special "Slinky" type forming tools, which are impractical in small quantity production. Similarly, forming the baffles integral with the chamber walls by machining or otherwise deforming a cylindrical solid would be very tedious and costly, but would be an alternative way to produce the baffles.

Figure 3A:
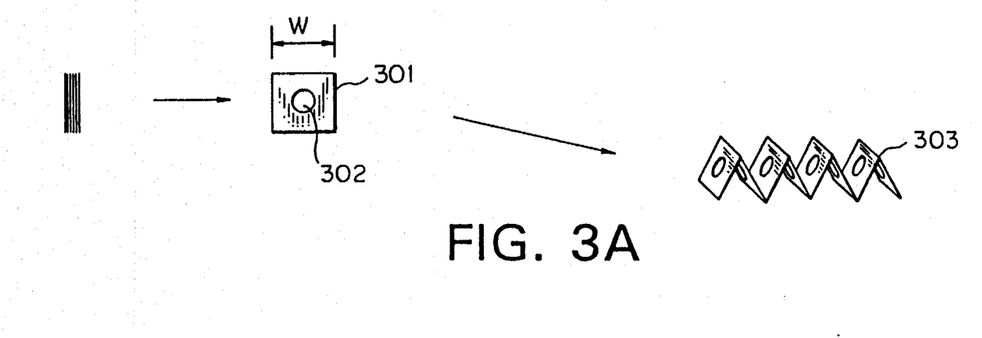
FIGS. 3A-B illustrate manufacture of an alternate light trap for the optical smoke monitor of the present invention.
Figure 3B:
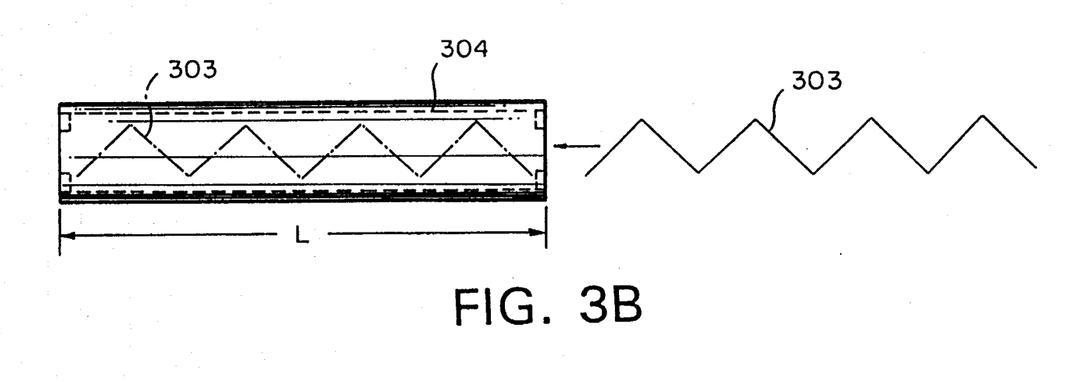
Figure 3C:
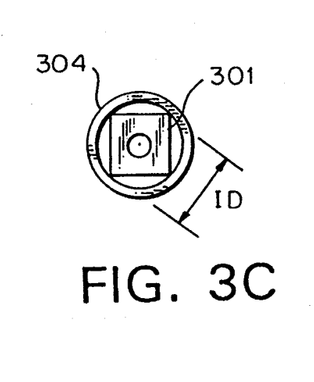
FIG. 3C is a front view of FIG. 3B.

FIGS. 3A–C show another baffling means that can be used in the present invention. This baffling means 303 uses a thin (generally, about 0.01 inch thick) strip of metal such as aluminum 301 folded into an accordion shape, pressed flat, punched to form concentric holes 302 through each layer, and then extended 303 such that the panels slope at about 45 degrees with respect to the light path. The slope of the accordion panels affects the positioning of the optical baffling panels along the length of the chamber while generating an increased flow area between the straight edges of the panels and the circular inside wall of the chamber. Stretching seven panels, each about 0.75 inch high with a hinged edge about 0.38 inch across the 4.1 inch chamber length resulted in each panel being angled about 50 (+/−10) degrees with respect to the center line of the chamber. Eliminating one panel decreased the angle and canted the central hole severely. Adding a panel increased the angle, but did not improve performance.

The seven panel version was easy to fabricate and performed as well as the nine half washer baffle described above, but was much easier to fabricate. The sloping of the panel created an elliptical center light aperture, which was not ideal considering the symmetrical beam of the LED. Therefore, the central light aperture was double punched in the flattened state, one punch offset from the other, so that when expanded in the chamber, the light aperture was nearly circular. An elliptical punch would generate a perfect hole such that, when the stack is expanded, the aperture is truly circular. A double offset punch provided the same effect. Other cross sectional shapes can be used, particularly a shape with concave cutouts on the vertical sides which would increase the flow area without compromising the baffling function. A circular panel would not work as well, as this would minimize the desired airflow enhancement. Screen type baffles formed similarly to the half disks or accordion sheet metal versions would initially enhance flow area, but were deemed to be susceptible to blockage from dust accumulations, thus continuing to arrive at better baffle configurations.

The baffles as shown are substantially rectangular in cross section but any cross-sectional configuration can be used which reduces dust accumulation while not unduly minimizing airflow. The baffle means 303 is inserted into tubing 304, and the corners of the baffle means are glued to the inside of the tubing. When the baffles in the tubing 304 are inserted inside the optical chamber 2, the air flow areas between the flat edges and the interior arc of the circular optical tube was sufficient to reduce the smoke access time from 30 minute to 30 seconds. Moreover, this baffle arrangement is easily manufactured from a strip of thin aluminum metal, folding and punching the metal, and extending the metal. The baffle means was easily installed inside the tube 304 using epoxy adhesive applied to the corners of the baffle before inserting the extended metal baffle inside the tube. The inside of the tube 304 was subsequently spray painted with flat black paint to coat substantially all of the tube wall and baffle components. The resulting baffle substantially eliminated any extraneous light transmission except directly through the open center of the baffle means. The air flow area was reduced to about 50% of the total cross section, which only slightly improved the smoke access time, but vastly reduced manufacturing time as compared with the half disks shown in FIGS. 2A–2F. The aluminum used, 0.01 inch thick, was thinner than the 0.05 inch thick washers, so, unless the edges are sharpened, the circular internal edge surfaces have 1/5th the amount of surface area exposed to the optical beam for dust accumulation and reflection. Therefore, the sensitivity to dust was reduced substantially. Any dust that did enter the optical tube and deposit within the optical chamber fell harmlessly between the central baffle edges and out of optical range.

The orientation of the optical components in line with the removable caps permitted easy cleaning of any buildup of dust or film on the surfaces of the optical devices, both LED's and photo transistors, from time to time simply by removing caps 14 an 15 and inserting a tube brush of approximately the same diameter as the inner diameter of the tube. A few brush strokes restore the tube to factory new condition. It is also possible to wash the baffle means with detergent and water. The brush can be stowed inside the enclosure along the left-rear edge, and attached by string or wire for security.

It is essential that the optical smoke monitor be capable of field calibration. Conventional ionizing type smoke detectors are not cleanable, and on site calibration is virtually impossible without a smoke gallery. As this would be impractical, a unique calibration means was developed for the optical sensor of the present invention. This comprises a filter 30 made of a thin, rigid, transparent film attached to the right cap 15. Rotating the cap 90 degrees to the "calibrate" position indicated with a label places this optical filter material directly into the light beam, making photo transistor 11 indicate a reduced light level and simulating a full scale level of smoke. Because this simulates an actual smoke condition, physical and electrical, this constitutes a full test of the optical and electronic systems, thus permitting the instrument to be calibrated in the field, assuring continued and easily verified accuracy.

The zero smoke setting is more easily handled, as the output is simply set to read 4 ma (zero smoke) when there is no visible ambient smoke in the area. A flash light beam in a darkened room where the sensor is mounted shows if the air is clear of dust and smoke.

Electrical Circuitry for the Smoke Monitor

Figure 4:
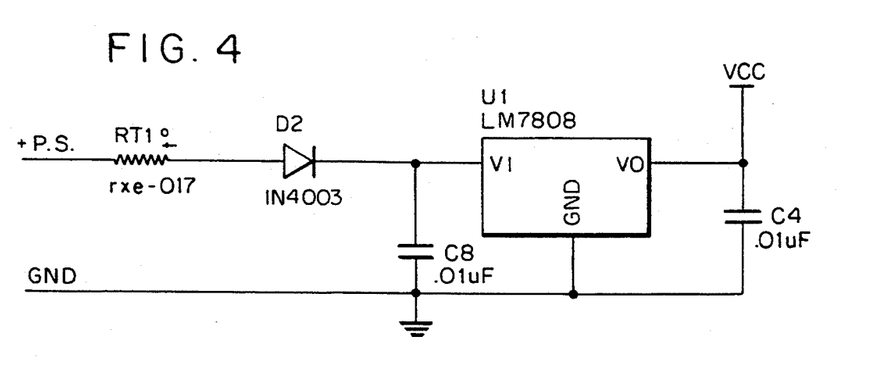
FIG. 4 is a schematic of the power supply to the smoke detector.
Figure 5A:
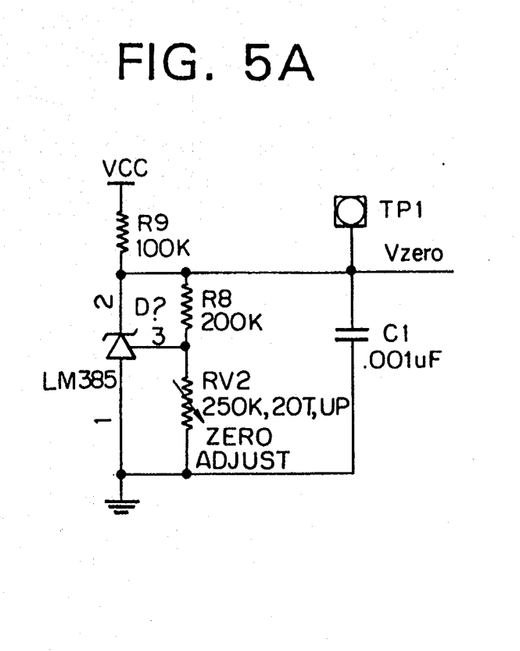
FIGS. 5A-F show voltage references of the schematic of the present invention.
Figure 5B:
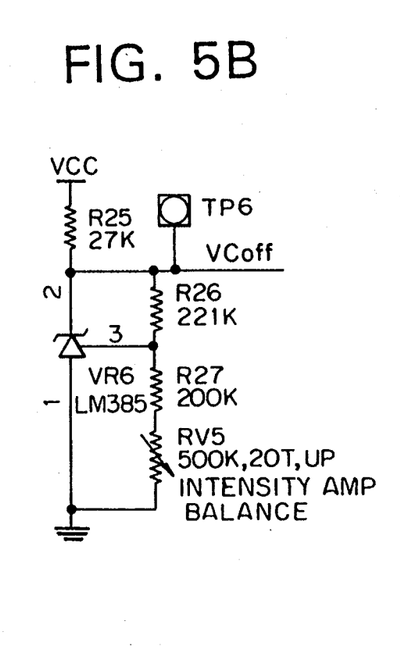
Figure 5C:
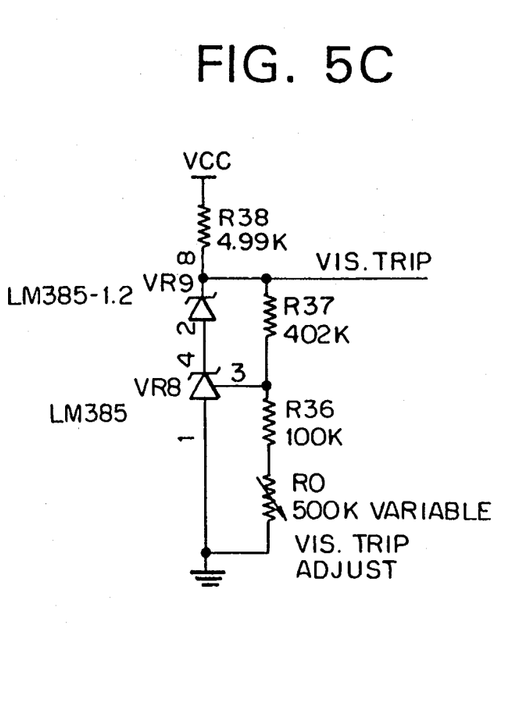
Figure 5D:
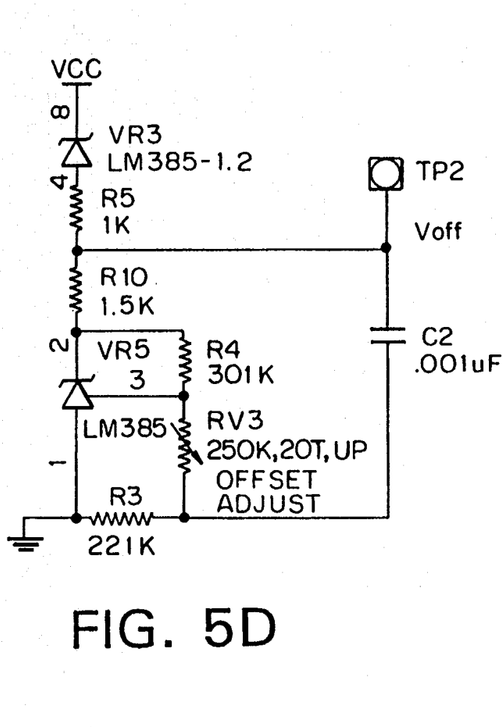
Figures 5E, 5F:
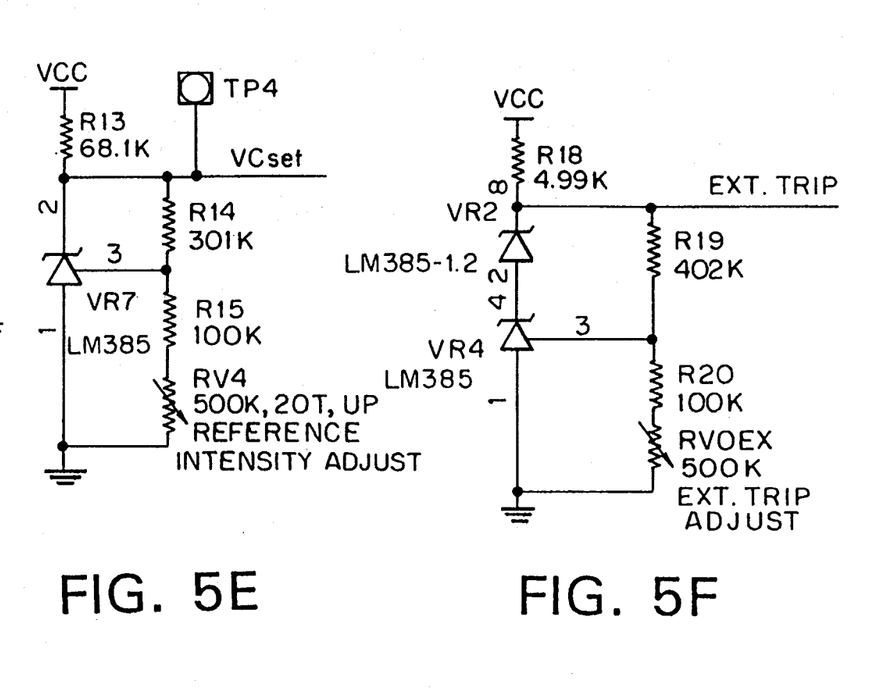

Referring to FIG. 4, the power supply in the smoke monitor of the present invention uses a circuit which converts a 10–30 VDC input to a regulated 8 VDC output. The input is protected against reverse polarity by diode D2. A positive coefficient thermistor (RT1) on the input stage is used to provide over current protection. Final DC regulation is achieved by $U_1$ voltage regulator. Capacitors C4 and C8 are used to achieve improved regulator stability.

The voltage references for the smoke monitor of the present invention are shown in FIGS. 5A–5F. All amplifier and circuit voltage references were generated using the National Semiconductors LM385 Series Micropower voltage references. The LM 385 series was chosen for its low power consumption, stability, and low output impedance. However, any similar voltage reference device which works substantially the same can be used.

The amplifier reference voltage $V_{off}$ was designed to track $V_{cc}$. This was done so that the output current (4–20 ma) would be independent of changes in $V_{cc}$. This was achieved by setting the gain of amplifier U2B equal to the inverse gain of the voltage divider circuit created by resistors R5 and R10.

Figure 6:
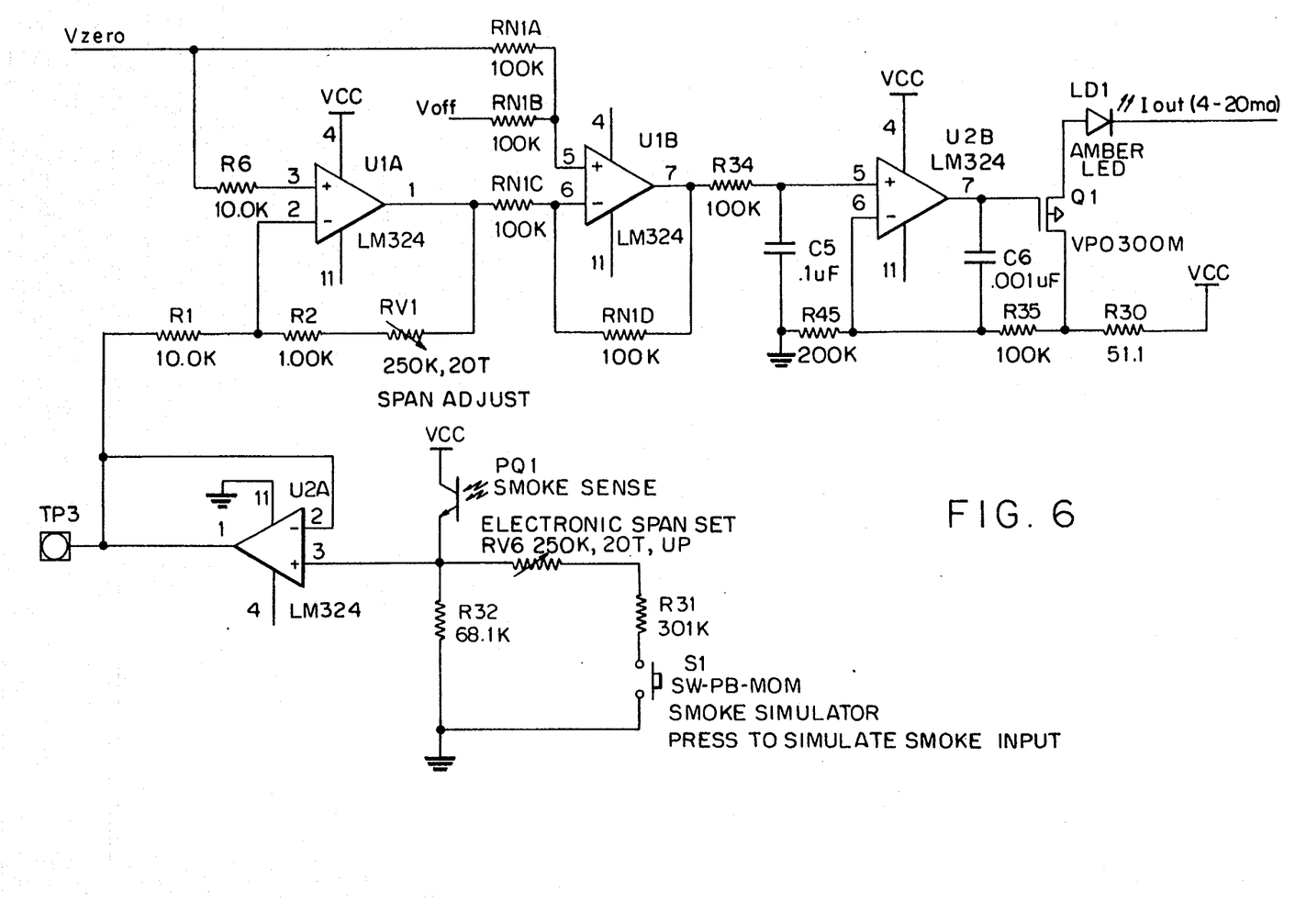
FIG. 6 shows the signal amplification and 4-20 ma electrical analog signal driver of the present invention.

FIG. 6 shows the smoke signal amplification used in the smoke monitor of the present invention. Photo transistor PQ1 produces a current flow proportional to the IR-intensity at the receiving lens. This current creates a voltage across drop resistor R32. In an environment which is free of smoke and dust, this voltage is equal to $V_{zero}$ which is set during a setting of amplifier U1A. Calibration is effected by adjusting potentiometer RV2 accordingly. Under smoke and dust conditions, the IR-intensity at the receiving lens decreases in proportion to the density of the smoke and dust. This decrease in intensity causes the current in photo transistor PQ1 to decrease, thus decreasing the voltage drop across resistor R32. This change in voltage is then amplified by amplifier U1A. Potentiometer RV1 adjusts the gain of the amplifier.

Amplifier U1B sums the offset voltage $V_{off}$ with the difference of the amplified signal minus the zero voltage ($V_{zero}$). This provides the offset necessary to generate a signal of 4 ma under conditions of no smoke.

FIG. 6 also shows the 4–20 ma output drive. A P-channel mosfet is used in conjunction with amplifier U2B to convert the voltage signal to a 4–20 ma current output. A gain of 1.5 is necessary at this stage because of the limited voltage swing of the amplifier.

Figure 7:
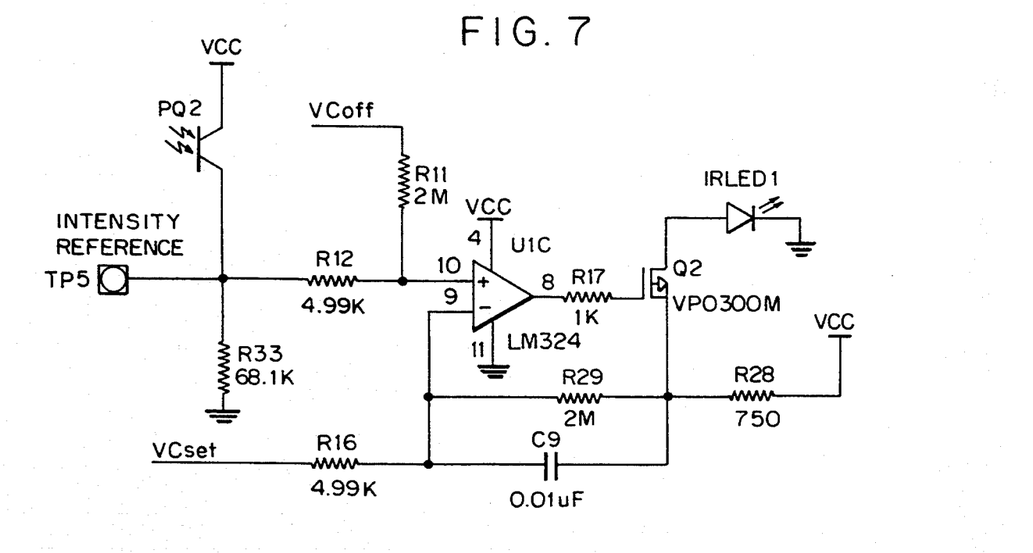
FIG. 7 shows the intensity compensation for the infrared LED light source.

FIG. 7 shows the intensity compensation circuit, which maintains a constant output of the IR-LED1 as a function of the photo transistor PQ2. Photo transistor PQ2 is oblivious to smoke because of its close proximity to the IR-emitter, thus providing an accurate reference.

Photo transistor PQ2 produces a voltage output across resistor R33 proportional to the intensity of the IR-emitter. As the intensity begins to drop, the voltage across resistor R33 will begin to decrease. The circuit detect this decrease in voltage and subsequently will increases the intensity until the voltage across resistor R33 is at its original set value. This is accomplished by using a non-inverting differential amplifier U1C in conjunction with a voltage to current convertor used to drive the IR-LED. The original voltage output can be set by adjusting the $V_{cref}$ to its desired value (2.50 V DC).

Smoke gallery tests were conducted using white talcum powder to simulate dust. These tests showed complete elimination of reflected light, as evidenced by a vast reduction of sensitivity to the powder (dust). Although this configuration of the baffle means was very effective in minimizing the effects of dust, the assembly of the half disks into slots in an auxiliary holding tube was very tedious and labor intensive.

Field calibration should be conducted in clear air, i.e., air in which there is little smoke or dust. If clean conditions cannot be obtained on the site where the smoke monitor is located, the monitor should be removed to a clean area for calibration.

For zero adjustment, the calibration cap 15 is set in the "run" position. A hand held multimeter is connected to monitor the 4–20 ma output. A 3.1 mm phono plug, engaged in the jack provided with an external multimeter, can be used to read the signal current, once the meter is set to the proper milliamp scale. After stabilizing, the zero pot is slowly adjusted to obtain a precise output of 4 ma. Turning the pot clockwise increases the output current. If the output gives an upscale reading and cannot be adjusted to 4 ma, the optical sensors may be contaminated and require cleaning, as described above.

For smokeless span adjustment, the calibration cap is rotated to the "calibrate" position. This introduces a filter into the optical path to simulate the 10% obscuration per meter standard. The span pot is then adjusted to read precisely 20 ma output. This sets the smoke monitor for a 20 ma output at approximately 10% smoke obscuration. The calibration cap is rotated back to the "run" position.

Federal regulations for fire monitoring, 30 CFR 75, require periodic functional tests between calibration events. A test switch which operates by pushing or other means is incorporated. This switch introduces a calibrated resistance in series with the main photo transistor 11 which makes the circuit output go to full scale or any other value as may be prescribed and factory set. This is shown in FIG. 7 of the schematic.

The electronic circuit board 20 is potted in an epoxy matrix forming a solid block 28 measuring approximately 2.5 inches×3.5 inches×0.6 inch. In one method of production, pigtail leads extending from the external connections are consolidated into a six-pin connector 32. An amber LED glows on the block to indicate when power is applied and the signal output is functional. The implementation of all features, including two external alarm connections, results in a multi-pin connecter installed directly on the potted circuit module. Four potentiometers are used to set the LED intensity, balance the photo transistor bridge, adjust the zero smoke setting, and to adjust the full scale setting. Two additional potentiometers are optional. These optional potentiometers can be used for setting the threshold levels of the two alarm outputs.

Still another potentiometer and a test switch are shown on the electronic module 20 and on the schematic. Depressing the push-button introduces a resistance in the photo-transistor circuit to simulate a smoke condition. The adjacent potentiometer adjusts the amount of resistance, and thereby provides a means to calibrate the effects of the test switch to whatever output is desired.

The package design of the smoke monitor of the present invention is unique in that the entire optical and flow control assembly rotates around the access ports 3 and 4. The device may be housed in a metal or other rigid box 40. The device is attached near the access ports to the housing 40 and can rotate downwardly as shown by the arrow in FIG. 1B.

The electronics module is carried on a backplate, situated to conserve space between the four sides of the optical/flow assembly, providing good access for adjusting the potentiometers. Clamp 13 secures the optical chamber in the stowed position. A hinged lid (not shown) covers the unit. A digital meter may be installed on the enclosure lid to monitor the 4–20 ma output and continuously display the obscuration level 0–10% per meter. Alarm means such as a horn and/or strobe light can be attached to the enclosure to provide visual and/or audible alarms.

Using the light beam absorption of the present invention, the output of the device of the present invention correlates precisely with the MSHA specifications and is nonambiguous.

In addition to providing more comprehensive fire detection than carbon monoxide sensors, optical smoke monitors avoid nuisance false alarms from diesel equipment and from interfering gases. MSHA field inspectors can recommend smoke sensors to replace or supplement carbon monoxide sensors where low carbon monoxide fires are possible or where false carbon monoxide alarms are frequent. Electrical equipment may use either carbon monoxide or smoke sensors.

The device of the present invention relies upon a combination of optical and mechanical designs with electronic circuitry to compensate for temperature changes and to correct for film or dust deposited onto the optical surfaces. If the device ever runs out of the adjustment range, the optics can be cleaned.

The analog signal of the detector ranges from about 4 ma in clear air to 20 ma at 10% per meter obscuration. Although it is possible to use a higher range for smoke detection in, for example, a mine environment, the use of a higher range would put the 5% alarm point lower down the scale, which is not ideal for accuracy or sensitivity. However, for monitoring environments in which much higher densities of smoke are present, such as for monitoring stack emissions, the range should be increased proportionately to the amounts of smoke to be detected. The upper limit to the range to be used is adjusted relative to the intensity of the LED light source.

The device is generally set to trigger an alarm at 3–5%, with an optional early warning indication set at 2%. A test jack provides easy access for connecting the 4–20 ma signal to an external milliammeter without disconnecting the computer link.

A built in optical filter provides a field calibration reference, thus avoiding the need for a smoke source. This also is the means for conducting the 31-day calibration test required by the Mine Safety and Health Administration (MSHA). The zero smoke point is set when ambient air is clear by shining a light beam down the entry to the optical filter without a halo. To simulate full scale smoke, the optical filter cap is rotated into the calibrate position, and the span is adjusted to read 20 ma.

In addition to more comprehensive fire detection than carbon monoxide sensors, optical smoke monitors avoid nuisance false alarms from diesel equipment and from interfering gases.

The foregoing description of the specific embodiments will so fully reveal the general nature of the invention that others can, by applying current knowledge, readily modify and/or adapt for various applications such specific embodiments without departing from the generic concept, and, therefore, such adaptations and modifications should and are intended to be comprehended within the meaning and range of equivalents of the disclosed embodiments. It is to be understood that the phraseology of terminology employed herein is for the purpose of description and not of limitation.

What is claimed is:

1. An optical smoke monitor comprising a housing enclosing a smoke monitoring chamber;
   two access ports located opposite each other on the housing;
   a shunt flow path located between said two access ports;
   means to conduct air from said access ports vertically upwardly to an optical chamber having a first end and a second end;
   a light source at the first end of said optical chamber, which light source produces a light beam axially through of said optical chamber;
   radiation sensing means at the second end of said optical chamber to receive the light beam and issue an electrical signal proportional to the received light intensity to an electronic module;
   whereby the electronic module provides variable electronic output, generating an output essentially proportional to the optical obscuration caused by the smoke.

2. The optical smoke monitor according to claim 1 wherein a second radiation sensing means is located near said first end of said optical chamber to monitor the optical intensity of the light beam emitted from the light source and connected to electronic circuitry;
   and the electronic circuitry receives a signal from said second radiation sensing means and controls the current to maintain a constant light level.

3. The optical smoke monitor according to claim 1 wherein optical baffle means are provided within the optical chamber.

4. The optical smoke monitor according to claim 3 wherein said baffle means have the form of half disks.

5. The optical smoke monitor according to claim 3 wherein said baffle means are in the configuration of an accordion.

6. The optical smoke monitor according to claim 1 further including a right vertical flow stack at the right side of said optical chamber and a left vertical flow stack at the left side of said optical chamber.

7. The optical smoke monitor according to claim 6 wherein said right vertical flow stack is provided with a closure device and said left vertical flow stack is provided with a closure device.

8. The optical smoke monitor according to claim 7 wherein each said closure device is a friction-fit cap.

9. The optical smoke monitor according to claim 7 wherein a filter is attached to the closure device of said right flow stack whereby moving said closure device 90 degrees to a calibrate position indicated with a label places said filter directly into the light beam of said first photo receiver whereby a reduced light level is indicated.

10. The optical smoke monitor according to claim 1 further including an amplifier voltage reference means to monitor voltage output of the electronic circuitry.

11. The optical smoke monitor according to claim 1 wherein the light source is a light emitting diode.

12. The optical smoke monitor according to claim 1 wherein the radiation sensing means is a photo transistor.

13. The optical smoke monitor according to claim 1 wherein the zero setting of an amplifier for the radiation sensing means is the voltage when there is no smoke or dust in the optical chamber.

14. The optical smoke monitor according to claim 1 further including a second radiation sensing means and located in close proximity to said light source and compensation circuit means for maintaining a constant intensity output of said second photoreceiver.

15. The optical smoke monitor according to claim 1 further including means to receive the analog output from the electronic module, which means to receive the analog output is located remote from the optical smoke monitor.

16. The optical smoke monitor according to claim 1 further including detection circuitry to monitor the level of said analog output.

17. The optical smoke monitor according to claim 16 wherein said detection circuitry is set from a location remote from said optical smoke monitor.

18. The optical smoke monitor according to claim 1 wherein said shunt flow path and said two access ports are attached to said housing in such a way that the shunt flow path and two access ports can be rotated downwardly.

19. The optical smoke monitor according to claim 1 wherein each of said two access ports expand immediately inside said ports to about double the diameter of each of aid two access ports to reduce the velocity of air flowing into each of said two access ports.

20. The optical smoke monitor according to claim 1 further including an external monitor for the electronic output from the electronic module.

21. The optical smoke monitor according to claim 20 wherein said external monitor generates alarms signals at a predetermined threshold and said external monitor is selected from the group consisting of meters, recorders, and computers.

22. The optical smoke monitor according to claim 21 wherein said predetermined threshold is 5% obscuration.

23. The optical smoke monitor according to claim 1 wherein said electronic module contains detection means for activating an alarm means.

24. The optical smoke monitor according to claim 23 wherein said alarm means is selected from the group consisting of horns, bells, and strobe lights.

25. The optical smoke monitor according to claim 1 including four potentiometers to set the intensity of the light source, to balance the radiation sensing means, to adjust a zero smoke setting an to adjust a full scale setting.

26. The optical smoke monitor according to claim 1 further comprising a dust plug for each of said two access ports.

* * * * *